United States Patent [19]

Kurosawa

[11] Patent Number: 4,497,313
[45] Date of Patent: Feb. 5, 1985

[54] FOOT BATH

[75] Inventor: Tadashi Kurosawa, Urawa, Japan

[73] Assignee: Tensho Electric Industrial Co., Ltd., Tokyo, Japan

[21] Appl. No.: 446,602

[22] Filed: Dec. 3, 1982

[51] Int. Cl.³ .............................................. A61H 7/00
[52] U.S. Cl. .................................. 128/24.1; 128/41; 128/66; 128/370; 128/395; 128/400
[58] Field of Search .................... 128/65–66, 128/24.1, 24 R, 41, 39, 25 B, 370, 395–396, 399–400; 604/291, 293, 20; D24/38, DIG. 10

[56] References Cited

U.S. PATENT DOCUMENTS

| | | | |
|---|---|---|---|
| 2,091,167 | 8/1937 | Solley | 128/66 |
| 3,045,100 | 7/1962 | Mills | 128/399 |
| 3,089,033 | 5/1963 | Fujisawa | 128/399 |
| 3,283,756 | 11/1966 | Turley | 128/66 |
| 3,366,105 | 1/1968 | Sadowski et al. | 128/25 B |
| 3,683,896 | 8/1972 | Peplin | 128/24.2 |
| 3,823,716 | 7/1974 | Borden | 128/65 X |
| 3,881,471 | 5/1975 | Grube | 128/25 B X |
| 3,965,495 | 6/1976 | McNair | 128/25 B X |
| 4,019,502 | 4/1977 | Elkins | 128/25 B X |
| 4,057,053 | 11/1977 | Kunz | 128/25 B |

Primary Examiner—Robert Hafer
Assistant Examiner—Chris Coppens
Attorney, Agent, or Firm—Wenderoth, Lind & Ponack

[57] ABSTRACT

A foot bath including a bath body for containing hot water, in which a foot is to be inserted, the bath body having a cover having an opening therein. A ceramic layer and a heater are provided in the cover so that the heater heats the ceramic layer to produce far infrared rays to irradiate the foot and hot water in the bath body. A structure is provided beneath the bath body for providing vibration to the foot. A pump is connected to the vibration structure so as to be driven thereby and an air transferring pipe is connected between the pump and the bottom of the bath body to transfer air therethrough while the air is heated by the far infrared radiation. A nozzle is provided in the bath body to mix the heated air and hot water and to eject the mixture of heated air and hot water at the surface of the hot water in a jet water stream.

5 Claims, 4 Drawing Figures

FOOT BATH

BACKGROUND OF THE INVENTION

1. Field of the Invention

This invention relates to a foot bath adapted to radiate far infrared rays to a foot for metabolism of a body to restore the body's energy and promote good health. More particularly, this invention relates to a foot bath adapted to massage a foot by means of a jet water generator and excite or stimulate the foot by means of a vibrator.

2. Prior Art

A foot has many vital points identified in oriental medical science which are closely related with various internal organs. It is well known that stimulation of the vital points of the foot causes fatigue such as stiffness in the shoulders to be relieved and the internal organs and the nervous system to be restored.

More than 60% of the body's blood is collected in the legs. Accordingly, since a person leads an active life while standing up for a long time, the body parts where congestion tends to occur include the legs. Thus, it is known that making ageing begins in the feet.

Also, feet which are closed by socks or shoes to be prevented from breathing and tend to become among the most dirty of the various parts of the body and to have the most unnatural stress applied thereto. This causes fatigue to be promoted and the internal organs to be adversely effected. Although the feet are the most important parts of the body as noted from the foregoing, people has an indifference toward the feet. Conventionally, there have been developed many complicated and expensive instruments which are adapted to stimulate the shoulder or the back of the body. However, there have been developed only simple instruments such as a foot stimulation mat or a foot stepping bamboo device for stimulating the foot.

SUMMARY OF THE INVENTION

Accordingly, it is a principal object of the invention to provide a foot bath adapted to clean, massage and also practice a finger-pressure treatment upon a foot to promote circulation of the blood, breathing of the skin and stimulation of the vital points.

It is another object of the invention to provide a foot bath adapted to radiate far infrared rays to the foot to promote metabolism of the body, which has an excellent medical effect as noted recently.

It is another object of the invention to provide a foot bath adapted to apply a jet of water and vibration to stimulate the foot and also to rhythmically restore the autonomous nerve system from a disorder which tends to occur due to nerve strain.

It is a further object of the invention to provide a foot bath adapted to most effectively apply a water jet to the foot.

It is a still further object of the invention to provide a foot bath adapted to stimulate the back of the foot when it is placed in the foot bath.

In accordance with the invention, there is provided a foot bath which includes a bath body for containing hot water and receiving the foot therein, the bath body having an openable cover. The cover is provided with a ceramic layer and a heater for heating the ceramic layer so as to produce far infra-red radiation to be radiated to the foot and hot water in the bath body. Structure is provided under the bath body for providing vibration to the foot. A pump is connected to the vibration structure so as to be driven thereby and an air transferring pipe is connected between the pump and the bottom of the bath body to transfer air from the pump to the bottom of the bath body while the air is being heated by the far infra-red radiation. A nozzle is provided in the bath body to mix the heated air and the hot water in the bath body to eject a jet water stream as a mixture of the heated air and hot water at the hot water surface.

BRIEF DESCRIPTION OF THE DRAWINGS

The above and other objects and features of the invention will be apparent from the description of a preferred embodiment taken along with reference to the accompanying drawings, in which.

DETAILED DESCRIPTION OF THE PREFERRED EMBODIMENT

Figure 1:
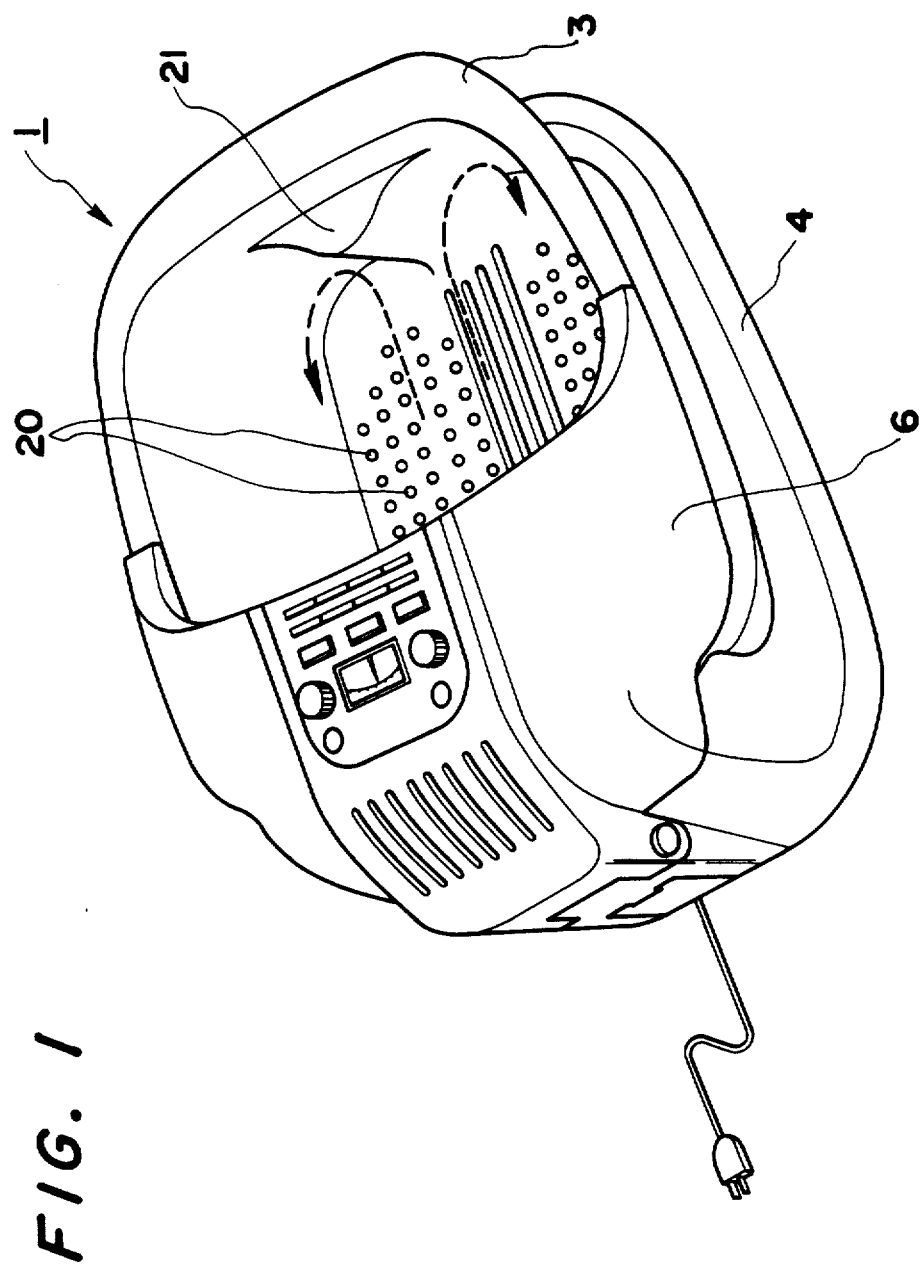
FIG. 1 is a perspective view of a foot bath constructed in accordance with an embodiment of the invention.

Referring now to FIG. 1, there is shown a foot bath 1 constructed in accordance with an embodiment of the invention. As shown in FIG. 1, the foot bath 1 comprises a bath body 3 containing hot water 2, which a foot 5 is to enter, a base 4 on which the bath body 3 is mounted, and a cover 6 provided on the bath body 3, in which an opening is formed through which the foot enters the bath body 3.

Figure 2:
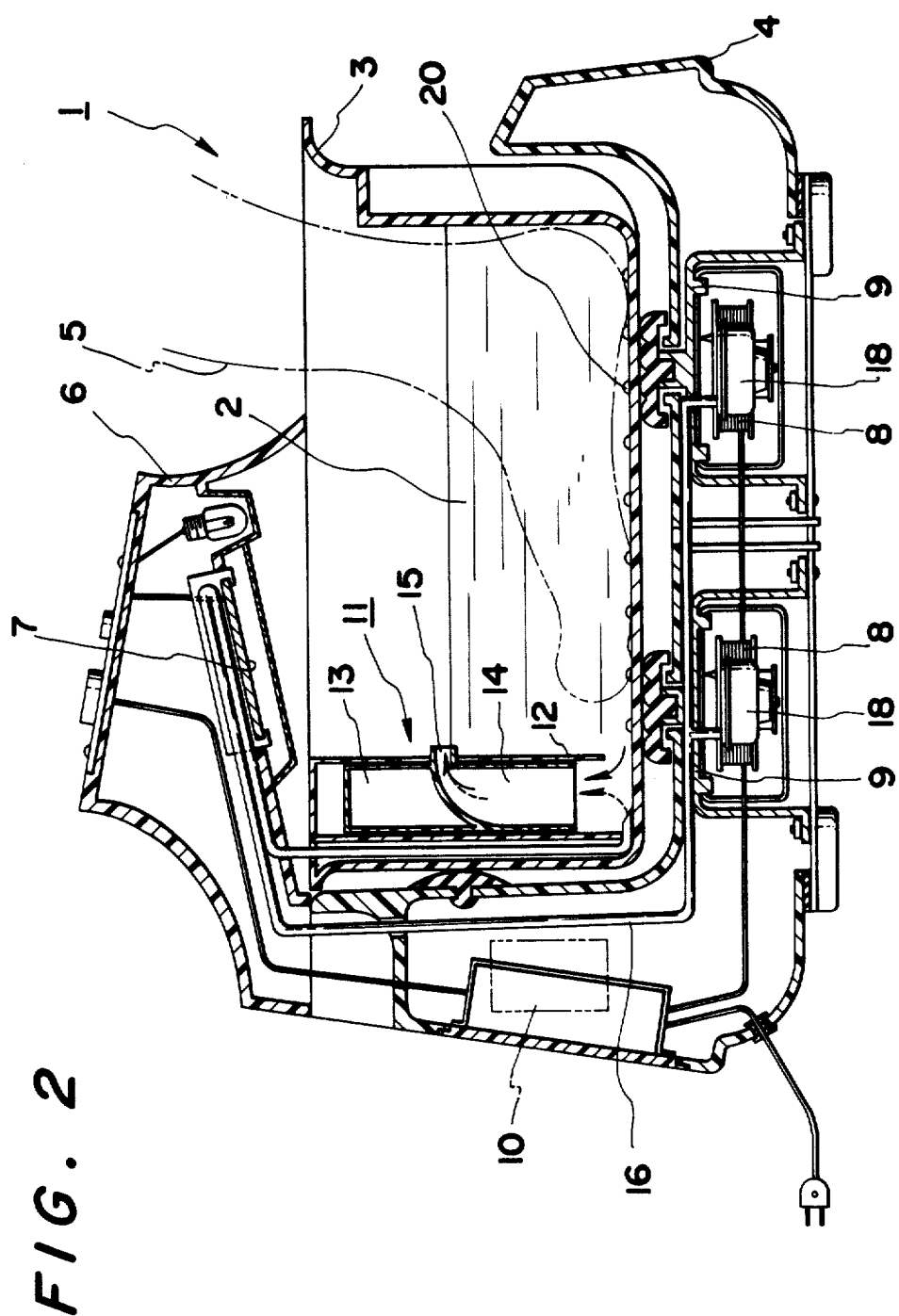
FIG. 2 is a cross-sectional view of the foot bath of FIG. 1.

Far infrared ray radiating means is provided in the cover 6. Referring to FIG. 2, the far infrared ray radiating means includes heating means not shown and a ceramic layer 7 mounted on the heating means so that the ceramic layer 7 is heated by the heating means. The heating means and the ceramic layer 7 are provided on the cover 6 so that the ceramic layer 7 faces the foot 5 in the bath body 3. Thus, it will be noted that the far infrared rays have a good effect on the foot 5 in the bath body 3. It should be noted that the far infrared rays having a wavelength longer than near and intermediate rays, have a better effect on the foot. It is known that ceramics to which heat is applied produce infrared rays having such a longer wavelength. It is also known that an oven used in the ceramic industry has a higher heating effectiveness because far infrared rays are reflected on the surfaces of the oven or of the ceramics. The hot water heated by the far infrared rays can deeply heat a body of a user to produce metabolism of the body because they have a secondary radiation and also cause a vibration of molecules.

The ceramics which produce such far infrared rays may be preferably ones which mainly comprise zirconium oxide or aluminium oxide. Such ceramics that mainly comprise zirconium oxide are known to be formed of zircon ($ZrO_2$ $SiO_2$) having additives of manganese oxide and oxides of iron, nickel and chromium. Such ceramics can radiate far infrared rays having a wavelength of 50 microns or greater.

It should be also noted that the far infrared rays reach the skin of the body at the depth of less than 5 mm so as to fully make the body warm. This causes the pores of the skin to be opened to excrete effete matter from the body. Although the water has a low temperature, it seems to the user that it has a higher temperature because the far infrared rays are applied thereto. Thus, it will be understood that the far infrared ray radiating means has a good effect of metabolism and excretion of effete matters which are caused by promotion of circulation of the blood without any load to the heart.

Vibrating means which includes two vibrators 8 are provided on the base 4 so that the bottom of the bath body 3 receives a vibration through a vibrating plate 9 to vibrate the foot 5 in the bath body 3. Thus, it will be noted that the foot 5 is stimulated by the vibrators 8 and given a rhythm which is generated by combination of pulsating sounds from the vibrators 8 controlled by control means 10. The vibrating means has an effect of restoration of the autonomous nerve system from a disorder which is caused by fatigue and especially nerve fatigue causing loss of rhythm of the body.

Figure 3:
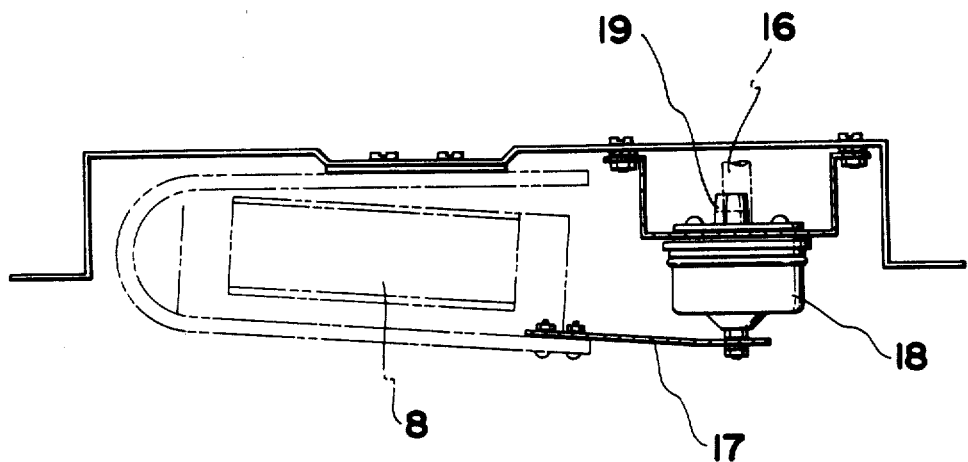
FIG. 3 is an enlarged side elevational view of an assembly of a vibrator and an air transferring pump.
Figure 4:
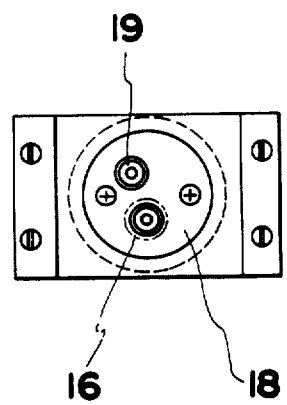
FIG. 4 is a front view of the air transferring pump of FIG. 3.

A jet water stream generating means 11 is provided at the front of the bath body 3 facing the tip of the toe. The jet water stream generating means 11 comprises a cylinder 12 in which an air-hot water mixture containing portion 14 having a vertically slidable float 13 is disposed. A nozzle 15 is provided at the upper portion of the mixture containing portion 14. The nozzle 15 is vertically slidable in the cylinder 12 in response to the quantity of hot water in the bath body 3 so that it is normally positioned nearly at the surface of hot water without sinking in the hot water or below the surface of hot water depending on variation in the quantity of hot water. Thus, it will be noted that the jet water is ejected at the surface of the hot water. The jet water stream generating means 11 also comprises an air transferring pipe 16 and pumps 18 having an ejection port connected to the air transferring pipe 16. The pumps 18 are connected through a plate 17 to the respective vibrators 8 as shown in FIG. 3. The pumps 18 may comprise a flexible diaphragm to vibrate in response to the motion of the plate 17 to feed air to the air ejection port. The air transferring pipe 16 passes through the portion of the cover 6 where the far infrared ray generating means is provided and opens at the lower opening of the cylinder 13 so that the air is heated by the far infrared ray generating means and is mixed with the hot water to eject jet of hot water containing foam from the nozzle to stimulate the foot 5. In FIG. 4, a reference numeral 19 designates an air inlet through which the air enters the pumps. The air inlet 19 has a check valve not shown provided therein. It will be noted that the heated air causes the hot water to be kept at its temperature.

As shown in FIG. 1, many warts 20 which are provided on the bottom of the bath body 3 serve to stimulate the foot 5 to promote metabolism of the body. As also shown in FIG. 1, a guide 21 which is provided at the rear portion of the bath body 3 serves to divide the stream of jet water from the nozzle 15 to circulate it so as to most effectively stimulate the sides of the foot.

As noted from the description of the embodiment, the far infrared rays from the far infrared ray generating means has an effect of metabolism on the foot while the stimulation of the foot is made by the vibration and the rhythm from the vibrating means and also by the undulation from the jet of foamy hot water. This causes the effect of metabolism and also of restoration of the body from fatigue. It should be noted that the division of the hot water jet by the guide at the rear of the bath body causes the whole foot to receive stimulation by undulation and a supply of oxygen to the skin of the foot to promote beautification of the skin to the body as well as metabolism, together with the aforementioned effects. It will be noted that the warts on the bottom of the bath body cause the back of the foot which has many vital points to be stimulated to promote the effects of metabolism and of restoration of the body from fatigue. It will be also noted that the jet stream has the effect of undulation on the foot at suitable places.

It should be noted that since the vibrating means for stimulation of the foot serves as a pump means to transfer the air through the air transferring pipe, a peculiar pump for transferring the air is not necessary to be provided inside or outside of the bath body. This prevents the foot bath from becoming large.

Although one preferred embodiment of the invention has been illustrated and described with reference to the accompanying drawings, it will be understood by those skilled in the art that various changes and modifications may be made without departing from the spirit and scope of the invention, which is intended to be defined only to the appended claims.

What is claimed is:

1. A foot bath comprising:
   a bath body for containing hot water, which a foot is to enter, said bath body having a cover having an opening therein;
   far infrared ray radiating means, provided in said cover, for radiating far infrared rays to the foot and the hot water, said radiating means including a ceramic layer in the cover and heating means for heating said ceramic layer to produce said far infrared rays;
   vibrating means, provided under said bath body, for providing vibration to the foot in said bath body;
   and means for generating a jet water stream in said bath body, said generating means, including a pump connected to said vibrating means so as to be driven by said vibrating means, an air transferring pipe connecting said pump and the bottom of said bath body to transfer air from said pump to the bottom of said bath body while the air is being heated by said infrared rays, and a nozzle provided in said bath body to mix the air heated by said infrared rays with the hot water in said bath body to eject the jet water stream as a mixture of heated air and hot water at the surface of the hot water in said bath body.

2. A foot bath as set forth in claim 1, wherein said jet water stream generating means is disposed so as to face a tip of a toe of said foot in said bath body.

3. A foot bath as set forth in claim 1, and further comprising a guide provided at the rear of said bath body to divide the jet stream toward the sides of the foot.

4. A foot bath as set forth in claim 1, further comprising many warts provided on the bottom of said bath body to stimulate the bottom of the foot.

5. A foot bath as in claim 1, wherein said cover is openably mounted on said bath body.

* * * * *